United States Patent
Heaton et al.

(10) Patent No.: US 9,238,024 B2
(45) Date of Patent: *Jan. 19, 2016

(54) METHODS FOR IMPROVING HEALTH IN CANINES

(71) Applicant: Quality IP Holdings, LLC, Carson City, NV (US)

(72) Inventors: Amy L. Heaton, Salt Lake City, UT (US); Mitchell K. Friedlander, Salt Lake City, UT (US); Dennis Gay, Salt Lake City, UT (US)

(73) Assignee: Quality IP Holdings, LLC, Carson City, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/301,256

(22) Filed: Jun. 10, 2014

(65) Prior Publication Data

US 2014/0295003 A1     Oct. 2, 2014

Related U.S. Application Data

(63) Continuation of application No. 13/623,111, filed on Sep. 20, 2012, now Pat. No. 8,747,923.

(51) Int. Cl.
| | |
|---|---|
| *A61K 36/53* | (2006.01) |
| *A61K 36/00* | (2006.01) |
| *A61K 47/00* | (2006.01) |
| *A61K 9/00* | (2006.01) |
| *A61K 9/14* | (2006.01) |
| *A61K 31/4015* | (2006.01) |
| *A61K 36/538* | (2006.01) |
| *A61K 31/198* | (2006.01) |
| *A23K 1/16* | (2006.01) |
| *A23K 1/18* | (2006.01) |

(52) U.S. Cl.
CPC .......... *A61K 31/4015* (2013.01); *A23K 1/1634* (2013.01); *A23K 1/1646* (2013.01); *A23K 1/1846* (2013.01); *A61K 9/0053* (2013.01); *A61K 31/198* (2013.01); *A61K 36/538* (2013.01)

(58) Field of Classification Search
CPC .................................................. A61K 36/538
See application file for complete search history.

(56) References Cited

U.S. PATENT DOCUMENTS

| | | | |
|---|---|---|---|
| 4,224,316 A | 9/1980 | Momany | |
| 4,745,124 A | 5/1988 | Ryan et al. | |
| 6,071,926 A | 6/2000 | Van Cauter et al. | |
| 6,346,264 B1 | 2/2002 | White | |
| 6,368,617 B1 * | 4/2002 | Hastings et al. | 424/439 |
| 6,517,832 B1 | 2/2003 | Marrongelle et al. | |
| 6,974,841 B1 | 12/2005 | Rapisarda | |
| 7,790,683 B2 | 9/2010 | Grasso et al. | |
| 8,551,542 B1 | 10/2013 | Heaton et al. | |
| 8,715,752 B2 | 5/2014 | Heaton et al. | |
| 8,722,114 B2 | 5/2014 | Heaton et al. | |
| 8,722,115 B2 | 5/2014 | Heaton et al. | |
| 8,734,864 B2 | 5/2014 | Heaton et al. | |
| 8,747,921 B2 | 6/2014 | Heaton et al. | |
| 8,747,922 B2 | 6/2014 | Heaton et al. | |
| 8,765,195 B2 | 7/2014 | Heaton et al. | |
| 2002/0165343 A1 | 11/2002 | Martinez et al. | |
| 2003/0068309 A1 | 4/2003 | De Simone | |
| 2004/0063608 A1 | 4/2004 | Mowrey et al. | |
| 2004/0122234 A1 | 6/2004 | Hauser et al. | |
| 2007/0286909 A1 | 12/2007 | Smith et al. | |
| 2008/0050777 A1 | 2/2008 | Buechler et al. | |
| 2010/0047364 A1 | 2/2010 | Moneymaker et al. | |
| 2010/0186121 A1 | 7/2010 | Unkefer et al. | |
| 2011/0052754 A1 | 3/2011 | Foley | |
| 2011/0081329 A1 | 4/2011 | Smith et al. | |
| 2014/0079822 A1 | 3/2014 | Heaton et al. | |
| 2014/0079823 A1 | 3/2014 | Heaton et al. | |
| 2014/0079830 A1 | 3/2014 | Heaton et al. | |
| 2014/0079832 A1 | 3/2014 | Heaton et al. | |
| 2014/0080887 A1 | 3/2014 | Heaton et al. | |
| 2014/0080888 A1 | 3/2014 | Heaton et al. | |
| 2014/0212388 A1 | 7/2014 | Prieto | |

FOREIGN PATENT DOCUMENTS

| | | |
|---|---|---|
| CN | 1243745 A | 2/2000 |
| GB | 9822333 | 12/1998 |
| KR | 1020000000757 A | 1/2000 |
| RU | 2429001 C1 | 9/2011 |
| WO | 9528854 A2 | 11/1995 |
| WO | 2004112511 A2 | 12/2004 |
| WO | 2007095618 A3 | 10/2007 |

OTHER PUBLICATIONS

Schoenherr et al. (2010) Am. J. Vet. Res., vol. 71, No. 8 pp. 934-939.*
Kim et al.; "Anti-Inflammatory Activity of Schizonepeta tenuifolia through the Inhibition of MAPK Phosphorylation in Mouse Peritoneal Macrophages," The American Journal of Chinese Medicine, vol. 36-No. 6, 2008, pp. 1145-1158.

(Continued)

*Primary Examiner* — Chris R Tate
*Assistant Examiner* — Russell Fiebig
(74) *Attorney, Agent, or Firm* — TraskBritt, P.C.

(57) ABSTRACT

A method of improving health in a canine includes administering to the canine a nutritional supplement comprising an amino acid secretagogue composition, which stimulates the pituitary gland of the canines to produce growth hormone. The nutritional supplement may be administered orally. The nutritional supplement may comprise L-arginine hydrochloride, Oxo-proline, L-lysine hydrochloride, and cysteine. When desired, the nutritional supplement may consist essentially of L-arginine hydrochloride, Oxo-proline, L-lysine hydrochloride, N-acetyl-L-cysteine, L-glutamine, and schizonepeta powder.

12 Claims, No Drawings

(56) References Cited

OTHER PUBLICATIONS

Anonymous, "Dr. Oz Human Growth Hormone HGH the Pursuit of Youth and Beauty," Oct. 13, 2011, retrieved from the internet: URL:http://healthybodydaily.com/dr-oz-in-case-you-missed-it/dr-oz=hgh-human-growth-hormone (retrieved on Sep. 15, 2014).

Anonymous, "Animal Outreach," Aug. 18, 2012, retrieved from the internet: URL: http://animal-outreach.org/2012/08 (retrieved on Sep. 15, 2014).

Extended European Search Report for application No. 13823912.4-1464/2744490, based on PCT/US2013060645, 4 pages.

Brigitte Mars. Internet Publication Date: Mar. 1, 2009 [Retrieved from the Internet on: Jul. 31, 2014]. Retrieved from: <URL: http://brigittemars.com/articles/herbal-natural-remedies/treating-headaches-naturally/>.

"MedlinePlus: L-arginine". Internet Archive Datae:Oct. 5, 2010 [Retrieved from the Internet on: Jul. 31, 2014]. Retrieved from: <URL: http://www.nlm.nih.gov/medlineplus/druginfo/natural/875.html>.

Bae, O.; "A Chinese medicinal composition for stimulating growth hormone", KR 2000/000757 A, 2000, Abstract Only.

Boger, R. H., "The Pharmacodynamics of L-Argininel-3", The Journal of Nutrition: 6th Amino Acid Assessment Workshop, 2007, pp. 1650S-1655S, vol. 137, American Society for Nutrition.

Chowen et al.; The regulation of GH secretion by sex steroids; European Journal of Endocrinology, 2004, pp. U95-U100, vol. 151, Society of the European Journal of Endocrinology.

Collier, S. R. et al., "Growth hormone responses to varying doses of oral arginine", Growth Hormone & IGF Research, 2005, vol. 15, pp. 136-139.

Cooper et al.; "Subclinical thyroid disease," Jan. 23, 2012, 13 pages.

Devesa et al.; "The Role of Sexual Steroids in the Modulation of Growth Hormone (GH) Secretion in Humans," J. Steroid Biochem. Molec. Biol., 1991,vol. 40-No. 1-3, pp. 165-173.

"External Wind", <http://www.tcvmherbal.com/JTDocs/Flyers/External%20Wind.pdf>, Downloaded from website Oct. 22, 2013, Jing Tang, 2 pages.

Farr et al.; "The antioxidants α-lipoic acid and N-acetylcysteine reverse memory impairment and brain oxidative stress in aged SAMP8 mice," Journal of Neurochemistry, 2003, vol. 84, pp. 1173-1183.

Fung, et al; "Schizonepeta tenuifolia: Chemistry, Pharmacology, and Clinical Applications," J. Clin. Pharmacal., 2002, vol. 42, pp. 30-36.

Gasco et al.; "Retesting the childhood-onset GH-deficient patient," European Journal of Endocrinology, vol. 159, 2008, pp. S45-S52.

Goto et al.; "Growth Hormone Receptor Antagonist Treatment Reduces Exercise Performance in Young Males", Sep. 2009, J Clin Endocrinol Metab, 94(9), pp. 3265-3272.

Grioli et al. "Pyroglutamic acid improves the age associated memory impairment," citation and abstract from Pyroglutamate, Jun. 13, 2002, Retrieved from the Internet on Apr. 9, 2013. Retrieved from: <http://web.archive.org/web/20020613031716/http://www.raysahelian.com/pyroglutamate.html>, 1 page.

Grunfeld et al.; "The Acute Effects of Human Growth Hormone Administration on Thyroid Function in Normal Men*," Journal of Clinical Endocrinology and Metabolism, 1988, vol. 67-No. 5, pp. 1111-1114.

Hansen et al.; Effects of 2 wk of GH administration on 24-h indirect calorimetry in young, healthy, lean men; Am. J. Physiol Endocrinol Metab 289: E1030-E1038, 2005.

Ho et al.; "The Pharmacokinetics, Safety and Endocrine Effects of Authentic Biosynthetic Human Growth Hormone in Normal Subjects", Clinical Endocrinology, 1989, vol. 30, pp. 335-345.

Kim et al.; "Anti-Inflammatory Activity of Schizonepeta tenuifolia through the Inhibition of MAPK Phosphorylation in Mouse Peritoneal Macrophages," The American Journal of Chinese Medicine, vol. 36-No. 6, pp. 1145-1158.

King, J.; "What is L-Arginine HCL?", <http://www.livestrong.com/article/464027-what-is-l-arginine-hcl/>, Jun. 5, 2011, 6 pages.

Leelarungrayub et al.; "N-Acetylcysteine Supplementation Controls Total Antioxidant Capacity, Creatine Kinase, Lactate, and Tumor Necrotic Factor-Alpha against Oxidative Stress Induced by Graded Exercise in Sedentary Men," Oxidative Medicine and Cellular Longevity. vol. 2011, Article ID 329643, 7 pages.

"L-Lysine," <http://www.ironmagazineforums.com/threads/149021-L-Lysine>, Retrieved from the Internet on: Jul. 15, 2014, 7 pages.

Maggi et al.; "Hormonal Causes of Male Sexual Dysfunctions and Their Management (Hyperprolactinemia, Thyroid Disorders, GH Disorders, and DHEA)," International Society for Sexual Medicine, 2012, 9 pages.

Mayo Clinic Staff; "Post-traumatic stress disorder (PTSD)," <http://www.mayoclinic.org/diseases-conditions/post-traumatic-stress-disorder/basics/definition/con-20022540>, Apr. 15, 2014.

Millea, P. J.; "N-Acetylcysteine: Multiple Clinical Applications," American Family Physician, Aug. 1, 2009, vol. 80-No. 3, pp. 265-269.

Moller et al.; "Effects of Growth Hormone Administration on Fuel Oxidation and Thyroid Function in Normal Man," Metabolism, vol. 41-No. 7, Jul. 1992, pp. 728-731.

Oliveira, et al.; "Free Amino Acids of Tronchuda Cabbage (*Brassica oleracea* L. var. costata DC): Influence of Leaf Position (Internal or External) and Collection time", Journal of Agricultural and Food Chemistry, 2008, vol. 56, pp. 5216-5221.

Pryor, et al.; "Growth Hormone: Amino Acids as GH secretagogues," <http://www.vrp.com/amino-acids/amino-acids/growth-hormone-amino-acids-as-gh-secretagogues-a-review-of-the-literature>, Retrieved Jul. 16, 2014, 5 pages.

Silber et al.; "Growth and Maintenance of Dogs Fed Amino Acids as the Source of Dietary Nitrogen," The Journal of Nutrition, Oct. 11, 1948, pp. 429-441.

Pavel et al.; "Impact of Growth Hormone on Central Nervous Activity, Vigilance, and Tiredness after Short-Term Therapy in Growth Hormone-Deficient Adults," Horm. Metab. Res., 2003, vol. 35, pp. 114-119.

PCT Search Report for International application No. PCT/US2013/060986, dated Dec. 27, 2013, 5 pages.

Pradines-Figueres et al.; "Transcriptional control of the expression of lipoprotein lipase gene by growth hormone in preadipocyte Ob1771 cells," Journal of Lipid Research, vol. 31, 1990, pp. 1283-1291.

Reid et al.; "N-Acetylcysteine Inhibts Muscle Fatigue in Humans," J. Clin. Invest., vol. 94, Dec. 1994, pp. 2468-2474.

Roddick, J.; "Sleep Disorders," <http://www.healthline.com/health/sleep/disorders#Overview 1>, Retrieved from the Internet on Jul. 16, 2014, 3 pages.

Rudman et al.; "The Short Child with Subnormal Plasma Somatomedin C1," Pediatric Research, vol. 19-No. 10, 1985, pp. 975-980.

Russell et al.; "Free Triiodothyronine has a distinct circadian rhythm that is delayed but parallels thyrotropin levels," J. Clin Endocrin Metab., Mar. 25, 2008, 22 pages.

Sahley, B J. "Amino Acid Brain Boosters" <http://www.teenlinkusa.com/aminoacids2.html>, Retrieved on Jul. 16, 2014, 4 pages.

Salomon et al.; "The Effects of Treatment with Recombinant Human Growth Hormone on Body Composition and Metabolism in Adults with Growth Hormone Deficiency," New England Journal of Medicine, Dec. 28, 1998, vol. 321-No. 26, pp. 1797-1803.

"Schizonepeta Tenuifolia," <http://examine.com/supplements/Schizonepeta+tenuifolia/>, Sep. 30, 2013, 12 pages.

Schwartz et al., "Hormone Replacement Therapy in the Geriatric Patient: Current State of the Evidence and Questions for the Future. Estrogen, Progesterone, Testosterone, and Thyroid Hormone Augmentation in Geriatric Clinical Practice: Part 1," Clin Geriatr Med vol. 27, 2011, pp. 541-559.

Schwartz et al., "Hormone Replacement Therapy in the Geriatric Patient: Current State of the Evidence and Questions for the Future. Estrogen, Progesterone, Testosterone, and Thyroid Hormone Augmentation in Geriatric Clinical Practice: Part 2," Clin Geriatr Med, vol. 27, 2011, pp. 561-575.

Sen et al.; "Exercise-induced oxidative stress: glutathione supplementation and deficiency," J. Appl. Physiol., vol. 77, 1994, pp. 2177-2187.

(56) References Cited

OTHER PUBLICATIONS

Sen et al.; "Oxidative stress after human exercise: effect of N-acetylcysteine supplementation," J. Appl. Physiol., vol. 76, 1994, pp. 2570-2577.

Sen, C. K.; "Glutathione homeostasis in response to exercise training and nutritional supplements," 1999, Molecular and Cellular Biochemistry, vol. 196, pp. 31-42.

Sevigny et al.; "Growth hormone secretagogue MK-677: No clincical effect on AD progression in a randomized trial," American Academy of Neurology, 2008, vol. 71, pp. 1702-1708.

Smith et al.; "Sleep Disorders and Sleeping Problems," <http://www.helpguide.org/life/sleep_disorders.htm>, Jun. 2014, Helpguide.org, 7 pages.

Tarantini et al.; "Serum ghrelin levels in growth hormone-sufficient and growth hormone-deficient patients during growth hormone-releasing hormone plus arginine test," J. Endocrinol. Invest. vol. 32, pp. 335-337, 2009.

Tavakkolizadeh et al.; "Effect of Growth Hormone on Intestinal NA+/Glucose Cotransporter Activity," Journal of Parenteral and Enteral Nutrition, vol. 25, No. 1, Mar. 2000, pp. 18-22.

Topo et al.; "The role and molecular mechanism of D-aspartic acid in the release and synthesis of LH and testosterone in humans and rats," Reproductive Biology and Endocrinology, Oct. 27, 2009, 11 pages.

Van Cauter et al.; "Metabolic consequences of sleep and sleep loss," Sleep Medicine 9 Suppl. 1, 2008, pp. S23-S28.

Van Liempt et al.; "Decreased nocturnal growth hormone secretion and sleep fragmentation in combat-related posttraumatic stress disorder; potential predictors of impaired memory consolidation," Psychoneuroendocrinology, 2011, vol. 36, pp. 1361-1369.

Vermeulen et al., "Testosterone, body composition and aging," J. Endocrinol. Invest., vol. 22, pp. 110-116, 1999.

Weikel et al.; "Ghrelin promotes slow-wave sleep in humans," Am J. Physiol Endocrinol Metab, vol. 284, pp. E407-E415, 2003.

Weizman et al.; "Impact of the Gulf War on the Anxiety, Cortisol, and Growth Hormone Levels of Israeli Civilians," Am J. Psychiatry, vol. 151-No. 1, Jan. 1994, pp. 71-75.

Welbourne, T. C.; "Increased plasma bicarbonate and growth hormone after an oral glutamine load 81-3," The American Journal of Clinical Nutrition, 1995, vol. 61, pp. 1058-1061.

Yen et al.; "Aging and the Adrenal Cortex," Experimental Gerontology, vol. 33, Nos. 7/8, pp. 897-910, 1998.

Yuen et al.; "Is Lack of Recombinant Growth Hormone (GH)-Releasing Hormone in the United States a Setback or Time to Consider Glucagon Testing for Adult GH Deficiency?", J. Clin, Endocrinol Metab, Aug. 2009, vol. 94-No. 8, pp. 2702-2707.

Alba-Roth et al.; Arginine Stimulates Growth Hormone Secretion by Suppressing Endogenous Somatostatin Secretion; Journal of Clinical Endocrinology and Metabolism, vol. 67, No. 6, 1988; 1186-1189.

Albert et al.; Low-Dose Recombinant Human Growth Hormone as Adjuvant Therapy of Lifestyle Modifications in the Management of Obesity; Journal of Clinical Endocrinology & Metabolism 89(2) 695-704; 2004.

Bernardi et al.; Somatotropic axis and body weight in pre-menopausal and post-menopausal women: evidence for a neuroendocrine derangement, in absence of changes of insulin-like growth factor binding protein concentrations; Human Reproduction vol. 12, No. 2 pp. 279-287, 1998.

Bidlingmaier et al.; Growth Hormone; Handbook of Experimental Pharmacology 195; 2010; pp. 187-200.

Bjorntorp, et al.; Hypothalamic Origin of the Metabolic Syndrome X; Annals New York Academy of Sciences, pp. 297-307; 1999.

Bjorntorp, P.; Do Stress reactions cause abdominal obesity and comorbidities?; The International Association for the Study of Obesity, Obesity reviews; 2 73-85; 2001.

Bjorntorp, P.; The regulation of adipose tissue distribution in humans; International Journal of Obesity (1996) 20, 191-302.

Blackman et al.; Growth Hormone and Sex Steroid Administration in Healthy Aged Women and Men A Randomized Controlled Trial; JAMA, Nov. 12, 2002—vol. 288, No. 18; pp. 2282-2292.

Bredella, et al.; Peak Growth Hormone-Releasing Hormone-Arginine-Stimulated Growth Hormone iS Inversely Associated with Intramyocellular and Intrahepatic Lipid Content in Premenopausal Women with Obesity; J. Clin Endrocrinol Metab. Oct. 2009; 94(10): 3995-4002.

Carli et al.; Changes in the exercise-induced hormone response to branched chain amino acid administration; Eru. J. Appl. Physiology (1992) 64:272-277.

Chromiak et al.; Use of Amino Acids as Growth Hormone-Releasing Agents by Athletes; Nutrition 18:657-661, 2002.

Corpas et al.; Human Growth Hormone and Human Aging; Endocrine Reviews, vol. 14, No. 1; 1993; pp. 20-39.

Corpas et al.; Oral Arginine-Lysine Does not Increase Growth Hormone or Insulin-like Growth Factor-I in Old Men; Journal of Gerontology: 1993, vol. 48, No. 4, M128-M133.

Ding et al.; Novel serum protein biomarkers indicative of growth hormone doping in healthy human subjects; Preteomics 2011, 11, 3565-3571.

Fogelholm et al. Low-Dose Amino Acid Supplementation: No Effects on Serum Human Growth Hormone and Insulin in Male Weightlifters; International Journal of Sport Nutrition, 1993, 3, 290-297.

Gourmelen et al., Effet du chlorhydrate d'ornithine sur le taux plamatique de l'hormone de croissance (HGH); Annels D'Endocrinologie; pp. 526-528; 1972.

Hayes et al.; Recombinant Human Growth Hormone and Recombinant Human Insulin-Like Growth Factor I Diminish the Cataboloic Effects of Hypogonadism in Man: Metabolic and Molecular Effects; The Journal of Clinical Endocrinology & Metabolism; vol. 86, No. 5; 2001.

Hersch et al.; Growth hormone (GH)-releasing hormone and GH secretagogues in normal aging: Fountain of Youth or Pool of Tantalus?; Clinical Interventions in Aging 2008:3(1) 121-129.

Iranmanesh et al., Age and Relative Adiposity are Specific Negative Determinants of the Frequency and Amplitude of Growth Hormone (GH) Secretory Bursts and the Half-Life of Endogenous GH in Healthy Men; Journal of Clinical Endocrinology and Metabolism; vol. 73, No. 5; pp. 1081-1088.

Isidori et al.; A Study of growth hormone release in man after oral administration of amino acids; Current Medical Research and Opinion; vol. 7, No. 7, 1981; pp. 475-481.

Karlsson et al.; Effects of growth hormone treatment on the leptin system and on energy expenditure in abdominally obese men; European Journal of Endocrinology (1998) 138 408-414.

Kraemer et al.; Chronic Resistance training in women potentiates growth hormone in vivo bioactivity: characterization of molecular mass variants; Am. J. Physiol Endocrinol Metab 291: E1177-E1187, 2006.

Lambert et al.; Failure of Commercial Oral Amino Acid Supplements to Increase Serum Growth Hormone Concentrations in Male Body-Builders; International Journal of Sport Nutrition, 1993, 3, 298-305.

Legakis et al.; Human Galanin Secretion is Increased Upon Normal Exercise Test in Middle-Age Individuals; Endocrine Research 26(3), 357-365 (2000).

Maccario et al.; Relationships between IFG-I and age, gender, body mass, fat distribution, metabolic and hormonal variables in obese patients; International Journal of Obesity (1999) 23, 612-618.

Makimura et al.; The relationship between reduced testosterone, stimulated growth hormone secretion and increased carotid inima-media thickness in obese men; Clin Endocrinol (Oxf). Nov. 2010; 73(5): 622-629.

Menagh et al.; Growth Hormone Regulates the Balance Between Bone Formation and Bone Marrow Adiposity; JBMR; vol. 25, No. 4, Apr. 2010, pp. 757-768.

Merimee et al.; Arginine-Initiated Release of Human Growth Hormone; The New England Journal of Medicine; Jun. 26, 1969; pp. 1434-1438.

Nindl et al.; Growth hormone pulsatility profile characteristics following acute heavy resistance exercise; J. Appl Physiol 91: 163-172, 2001.

O'Connor et al.; Interrelationships of Spontaneous Growth Hormone Axis Activity, Body Fat, and Serum Lipids in Healthy Elderly Women and Men; Metabolism, vol. 48, No. 11 Nov. 1999: pp. 1424-1431.

(56) References Cited

OTHER PUBLICATIONS

Papadakis et al.; Effect of growth hormone replacement on wound healing in healthy older men; Would Repair and Regeneration Oct.-Dec. 1996; pp. 421-425.

Papadakis et al.; Growth Hormone Replacement in Healthy Older Men Improves Body Composition but Not Functional Ability; Ann Intern Med. 1996; 124-: 708-716.

Pasquali et al.; Hormones and pathophysiology of obesity; Hormones and Obesity; 2001 pp. 9-20.

Pelsers et al.; Influence of Gender in Growth Hormone Status in Adults: Role of Urinary Growth Hormone; Clinical Chemistry 45, No. 3, 1999, pp. 443-444.

Perry, Horace M. III; The Endocrinology of Aging; Clinical Chemistry 45:8(B); 1369-1376 (1999).

Rubin et al.; New anabolic therapies in osteoporosis; Current Opinon in Reeumatology 2002, 14:433-440.

Rudman et al.; Effects of Human Growth Hormone in Men over 60 Years Old; The New England Journal of Medicine; vol. 323, Jul. 5, 1990; 6 pages.

Su et al.; Insulin-like growth factor 1 and hair growth; 1999 Dermatology Online Journal; 20 pages.

Suminski et al.; Acute Effect of Amino Acid Ingestion and Resistance Exercise on Plasma Growth Hormone Concentration in Young Men; International Journal of Sport Nutrition, 1997, 7, 48-60.

Twickler et al.; Adult-Onset Growth Hormone Deficiency: Relation of Postprandial Dyslipidemia to Premature Atherosclerosis; The Journal of Clinical Endocrinology & Metabolism 88(6): 2479-2488.

Vance, Mary L.; Growth Hormone for the Elderly?; The New England Journal of Medicine; Jul. 5, 1990; pp. 52-54.

White et al.; Effects of an Oral Growth Hormone Secretagogue in Older Adults; J. Clin Endocrin Metab.; 2009; 29 pages.

Zouboulis et al.; Intrinsische Hautalterung; Eine kritische Bewertung der Rolle der Hormone; Hautarzt 2003 54: 825-832.

\* cited by examiner

METHODS FOR IMPROVING HEALTH IN CANINES

CROSS-REFERENCE TO RELATED APPLICATION

This application is a continuation/divisional of U.S. patent application Ser. No. 13/623,111, filed Sep. 20, 2012, which will issue as U.S. Pat. No. 8,747,923 on Jun. 10, 2014.

TECHNICAL FIELD

Embodiments of the present disclosure generally relate to methods and nutritional supplements for improving health in canines.

BACKGROUND

Growth hormone is an anabolic hormone capable of promoting linear growth, weight gain and whole body nitrogen retention in animals. Growth hormone is produced in somatotroph cells of the anterior pituitary gland of animals and secreted throughout life. It is mainly controlled in the brain by two hypothalamic peptides: growth hormone releasing hormone (GHRH), which stimulates its secretion and synthesis; and somatostatin, which inhibits them. In human beings and other mammals, regulated expression of the growth hormone pathway is considered essential for optimal linear growth, as well as homeostasis of carbohydrate, protein and fat metabolism.

As canines age, their growth hormone levels decrease considerably resulting in a loss of skeletal muscle mass, osteoporosis, increased fat deposition, decreased lean body mass, and other disorders. Studies in human beings and other mammals have demonstrated that the recombinant growth hormone therapy may address the reduction of growth hormone. However, the recombinant growth hormone therapy for canines is limited and has proved to be inefficient.

U.S. Pat. No. 7,361,642, issued on Apr. 22, 2008 to Draghia-Akli, discloses a method for increasing growth hormone in canines. A canine-specific growth hormone releasing hormone (dGHRH) or a nucleic acid molecule that encodes the dGHRH is administered to canines to increase the level of growth hormone secretion. The canines treated with specific growth hormone releasing hormone show increased insulin-like growth factor I, enhanced red blood cells production and hemoglobin concentration, and improved protein metabolism.

Journal of Orthopedic Research 15:519-527 (1997) discloses that a growth hormone secretagogue, MK-0677, elevates levels of serum insulin-like growth factor-I in canines, which in turn increases the size and strength of the quadriceps muscle in canines during remobilization.

U.S. Publication No. 2008/0119819, published on May 22, 2008 to Hojby, discloses that an administration of growth hormone enhances bone growth factors and fracture healing in canines.

It has also been reported that for adult canines of both sexes, exogenous growth hormone induces a marked increase in new bone formation. (Calcified Tissue Research 10(1):1-13 (1972)).

Other studies have shown that in the canines that were given growth hormone, the quantity of protein in the blood plasma is increased, and the plasma protein pattern is altered. (Endocrinology 53: 134-162 (1953)). Additionally, it is known that growth hormone treatment improves protein metabolism in canines.

SUMMARY OF THE DISCLOSURE

The present disclosure includes a nutritional supplement and a method of using the same for improving health in canines. The nutritional supplement is an amino acid secretagogue composition, which stimulates the pituitary gland of canines to release growth hormone.

A particular embodiment of the present disclosure relates to a nutritional supplement for improving health in canines, the nutritional supplement comprising L-arginine, Oxo-proline, and L-lysine.

Another particular embodiment relates to a nutritional supplement for improving health in canines, the nutritional supplement includes L-arginine hydrochloride, Oxo-proline, L-lysine hydrochloride, N-acetyl-L-cysteine, L-glutamine, and schizonepeta powder.

Other embodiments are drawn to methods of increasing growth hormone in canines, the methods including administering the disclosed nutritional supplement to a canine. In particular embodiments, the method includes orally administering the disclosed nutritional supplement to a canine.

DETAILED DESCRIPTION OF THE DISCLOSURE

The present disclosure relates to methods and nutritional supplements for improving health in canines. The nutritional supplement is an amino acid secretagogue composition, which stimulates the pituitary gland in a canine to produce growth hormone. Increased production of growth hormone in canines may prevent the loss of skeletal muscle mass, osteoporosis, increased fat deposition, decreased lean body mass, and other disorders. The supplement of the present disclosure may work as a dietary supplement by assisting the canine's ability to secrete growth hormone naturally in a manner which is safe and effective.

A particular embodiment of the present disclosure relates to a nutritional supplement for improving health of canines, the nutritional supplement including L-lysine, L-arginine, oxo-proline, and at least one of cysteine and glutamine. The supplement may additionally include both cysteine and glutamine and/or schizonepeta powder. In particular embodiments, a functional dosage may include L-arginine at a level between 0.1-6 mmol, oxo-proline at a level between 0.1-8 mmol, and/or the L-lysine in an amount between 0.1-12 mmol. The cysteine and/or glutamine may be contained at a level between 0.001-6 mmol. The cysteine may be n-acetyl L-cysteine, and the glutamine may be L-glutamine. The amino acids may be delivered as non-toxic salts thereof, effective complexes thereof, stable chelates thereof, active esters thereof, functional derivatives thereof, or mixtures thereof, which are effective to increase growth hormone levels in canines. The nutritional supplement may be present in an amount of 2.9 grams. Dosages are generally calculated in the range of about 20-50 gms per kg of body weight of the canine. The nutritional supplement may be administered to canines orally. The supplement may be in any acceptable and known oral formulation including, but are not limited to, powder, tablet, capsule, or liquid form.

Another particular embodiment relates to a nutritional supplement for improving health of canines, the nutritional supplement includes L-lysine HCl, L-arginine HCl, oxo-proline, N-acetyl L-cysteine, L-glutamine, and schizonepeta (aerial parts) powder. In particular embodiments, a functional dosage may include L-arginine HCl at a level between 0.1-6 mmol, and oxo-proline at a level between 0.1-8 mmol, and/or the L-lysine HCl in an amount between 0.1-12 mmol. The n-acetyl L-cysteine and/or L-glutamine may be contained at a level between 0.001-6 mmol. In another particular embodiment, a functional dosage may include L-arginine HCl at a level between 2.5-4.5 mmol, oxo-proline between 4-6 mmol, and/or the L-lysine HCl in an amount between 7-9 mmol. The n-acetyl L-cysteine and/or L-glutamine may be contained at a level between 0.001-0.5 mmol. The nutritional supplement may be administered to canines orally. The supplement may be in any acceptable and known oral formulation including, but are not limited to, powder, tablet, capsule, or liquid form.

Other embodiments are drawn to methods of increasing growth hormone in canines, the methods including administering the disclosed nutritional supplement to a canine. In particular embodiments, the method includes orally administering the disclosed nutritional supplement to a canine. The amount of dosage and frequency of administration may be varied according to many factors including, but are not limited to, canine breeds, ages (e.g., puppy, adult, elderly) and health of the canines.

The disclosed nutritional supplements may be administered to a canine to improve health, including by: increasing insulin-like growth factor I, enhancing red blood cells production and hemoglobin concentration, boosting protein metabolism, improving bone growth factors and fracture healing, increasing new bone formation, enhancing protein metabolism, or combinations thereof.

In accordance with the "consist essentially of" and "consisting essentially of" language, the nutritional supplement is essentially limited to the aforementioned ingredients and does not include any additional active ingredients intended to add nutritional content (e.g., vitamins, minerals, etc.), but may include additional ingredients not intended to add nutritional content such as ingredients intended to fulfill a non-nutritional purpose (e.g., coloring, fillers, flavoring, an ingredient for maintaining the structural form, etc.).

Each ingredient of the nutritional supplement may be prepared in accordance with any method known to one of ordinary skill in the art. Alternatively, each ingredient may be obtained in a fully prepared from a commercially available source.

The nutritional supplement may be in any suitable oral administration form, including but not limited to: a chewable form, a liquid form, a spray form, a capsule form, a suppository form, dissolvable wafer, and a powder form.

Irrespective of the structural form of the nutritional supplement, the ingredients of the nutritional supplement may be distributed homogeneously or non-homogeneously within the nutritional supplement.

The nutritional supplement may be administered to a canine on a regular basis, such as a weekly or monthly intake at a dosage tailored to the canine's needs; i.e., the nutritional supplement may be taken regularly as multiples (1×, 2×, etc.) of the structural units (pills, tablets, capsules, etc.) in accordance with the needs of the canine. For example, an elderly canine is likely to need higher daily doses than does a young canine. Alternatively, the nutritional supplement may be administered on an as-needed basis at a dosage tailored to the canine's needs, such as administering the nutritional supplement to the canine that is recovering from bone fracture. Veterinarian counseling may be beneficial for arriving at a desirable or optimal dosage tailored to the canine's needs.

The combination of types of amino acids, mass ranges, and specific formulations may be selected to be synergistically balanced and of adequate quantity to achieve the desired physiological effect, namely, growth hormone release. Improper combinations of the amino acids may be ineffective. The component amino acids are synergistic in the sense that several of them when combined together, synergistically stimulate the release of human growth hormone. The combination may also be chosen to reduce or inhibit chemical combination or reaction between the amino acids.

EXAMPLES

Example 1

The short-term effects of the disclosed supplement on the growth hormone level in canine are tested two hours after administration. The canine subjects are administered the capsules of supplement (SeroVital™) or an identical looking placebo. SeroVital™ is a blend of l-lysine HCl, l-arginine HCL, oxo-proline, N-acetyl-l-cysteine, l-glutamine, and schizonepeta (aerial parts) powder. Canine subjects are administered approximately 35 gms per kg of body weight. Blood is drawn at 15, 30, 60 and 90 and 120 minutes for assay. The growth hormone level is measured at each time point using the Siemens Immulite 2000 (intra-assay CV was 3.72%, inter-assay CV was 5.70%, and the detection limit for GH was 0.05 ng/ml). The 15 and 120 minute time points are additionally assayed for triiodothyronine (T3) as informative for mechanistic investigations.

The mean growth hormone in the canine subjects are increased more than 600% after the administration of supplement from 0.17 at baseline to 1.33 ng/ml at 120 minutes, while there is are no increases observed in the mean growth hormone of the canine subjects after the administration of placebo.

The growth hormone levels from baseline to 120 minutes (the growth hormone level at 120 minutes minus the growth hormone level at 0 minute), are increased about two fold when compared to the administration of a placebo. Overall, 120 minutes after the administration of the supplement, the growth hormone levels are significantly higher in absolute levels or by AUC.

Furthermore, the canines that were administered SeroVital™ will exhibit a deceased reduction in T3 by nearly one-half over the same time period, compared to the canines administered with the placebo. These results affirm that somatostatin inhibition plays a mechanistic role in the ability of SeroVital™ to induce significant increases in serum growth hormone levels in canine subjects.

These findings demonstrate that a specialized low-dose amino acid supplement can significantly increase short-term growth hormone levels in canines.

Example 2

The effect of the nutritional supplement on endurance and fat metabolism in canines are investigated. Each canine subject is measured for baseline weight, height, body fat percent and resting metabolic rate. Then, each canine subject is administered with the supplement SeroVital™, which is a blend of l-lysine HCl, oxo-arginine HCl, oxo-proline, N-acetyl-l-cysteine, l-glutamine, and schizonepeta (aerial parts) powder for 2 weeks before being measured again for weight, height, body fat percent and resting metabolic rate. The measurements before and after the administration of the supplement are analyzed.

Mean $VO_{2max}$ of the canine subjects increases compared to baseline. After the period of supplementation with SeroVital™, the mean RMR increases compared to baseline (P=0.165). Estimated daily calorie expenditure also increases.

After two weeks of supplementation with the supplement SeroVital™, both RMR and estimated daily calorie expenditure of the canine subjects tend to increase, evidencing the potential of the supplement to impart long-term fat burning effects. Additionally, endurance as measured by $VO_{2max}$ in the post-absorptive state significantly improves. Overall, the canine subjects administered with the SeroVital™ supplement will show enhanced parameters of endurance, energy, and vitality.

Example 3

The effect of the nutritional supplement on lean body mass and weight change of canines is studied. The canine subjects in the first group are given daily doses of the nutritional supplement for 6 months at different dosing concentrations of active ingredients, while the canine subjects in the second group are given placebo. Weight, percent lean body mass, and percent fat body mass are chosen as primary measures of body composition at the 6 month analysis period. The weight, body composition, and physical performance (including endurance) of the canine subjects are determined before and after the treatment, along with hormonal data analysis.

The canine subjects treated with the nutritional supplement show a sustained increase in lean body mass and an improved physical performance.

While embodiments of the present invention have been described herein for purposes of illustration, many modifications and changes will become apparent to those skilled in the art. Accordingly, the appended claims are intended to encompass all such modifications and changes as fall within the true spirit and scope of this invention.

We claim:

1. A method of increasing growth hormone in a canine in need thereof, comprising:
   providing a nutritional supplement, comprising:
      about 1 mmol L-arginine;
      about 1 mmol Oxo-proline;
      about 2 mmol L-lysine;
      about 1.5 µmol N-acetyl L-cysteine;
      about 2 µmol L-glutamine; and
      about 125 µg Schizonepta (aerial parts) powder; and
   administering an effective amount of the nutritional supplement to the canine.

2. The method of claim 1, wherein administering the nutritional supplement comprises orally administering.

3. The method of claim 1, wherein administering the nutritional supplement comprises administering about 2.9 grams of the nutritional supplement.

4. The method of claim 1, wherein the nutritional supplement is in powder, tablet, capsule, liquid, or wafer form.

5. The method of claim 1, wherein the nutritional supplement is administered once a week or once a month.

6. The method of claim 1, wherein the nutritional supplement is administered in an amount effective to reduce weight, increase endurance, increase fat metabolism, and/or increase lean body weight in the canine.

7. A method of increasing growth hormone in a canine in need thereof, comprising:
   providing a nutritional supplement, comprising:
      about 0.9 mmol L-arginine;
      about 1.3 mmol Oxo-proline;
      about 2.0 mmol L-lysine;
      about 1.5 µmol N-acetyl L-cysteine;
      about 1.7 µmol L-glutamine; and
      about 125 µg Schizonepta (aerial parts) powder; and
   administering an effective amount of the nutritional supplement to the canine.

8. The method of claim 7, wherein administering the nutritional supplement comprises orally administering.

9. The method of claim 7, wherein administering the nutritional supplement comprises administering about 2.9 grams of the nutritional supplement.

10. The method of claim 7, wherein the nutritional supplement is in powder, tablet, capsule, liquid, or wafer form.

11. The method of claim 7, wherein the nutritional supplement is administered once a week or once a month.

12. The method of claim 7, wherein the nutritional supplement is administered in an amount effective to reduce weight, increase endurance, increase fat metabolism, and/or increase lean body weight in the canine.

* * * * *